US012251701B2

(12) United States Patent
Ely et al.

(10) Patent No.: US 12,251,701 B2
(45) Date of Patent: Mar. 18, 2025

(54) FLUID THERMAL PROCESSING

(71) Applicant: HEWLETT-PACKARD DEVELOPMENT COMPANY, L.P., Spring, TX (US)

(72) Inventors: Hilary Ely, Corvallis, OR (US); Michael W. Cumbie, Corvallis, OR (US); Adam Higgins, Corvallis, OR (US); Rachel M. White, Corvallis, OR (US); Erik D. Torniainen, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 817 days.

(21) Appl. No.: 16/768,881

(22) PCT Filed: Oct. 3, 2018

(86) PCT No.: PCT/US2018/054265
§ 371 (c)(1),
(2) Date: Jun. 2, 2020

(87) PCT Pub. No.: WO2019/143392
PCT Pub. Date: Jul. 25, 2019

(65) Prior Publication Data
US 2020/0368750 A1    Nov. 26, 2020

Related U.S. Application Data

(63) Continuation-in-part of application No. PCT/US2018/013848, filed on Jan. 16, 2018.

(51) Int. Cl.
*C12P 19/34* (2006.01)
*B01L 3/00* (2006.01)
*B01L 7/00* (2006.01)

(52) U.S. Cl.
CPC ............ *B01L 7/52* (2013.01); *B01L 3/50273* (2013.01); *C12P 19/34* (2013.01); *B01L 2300/04* (2013.01); *B01L 2300/0663* (2013.01); *B01L 2300/0809* (2013.01); *B01L 2300/18* (2013.01); *B01L 2400/0406* (2013.01)

(58) Field of Classification Search
None
See application file for complete search history.

(56) References Cited

U.S. PATENT DOCUMENTS

| | | |
|---|---|---|
| 5,119,830 A | 6/1992 | Davis |
| 7,888,074 B2 | 2/2011 | Ehricht et al. |
| 7,892,819 B2 | 2/2011 | Wilding |
| 8,070,264 B2 | 12/2011 | Cornell et al. |
| 8,640,552 B2 | 2/2014 | Qasimi et al. |
| 9,102,511 B2 | 8/2015 | Ararao |
| 9,370,774 B2 | 6/2016 | Kumar |
| 2002/0197167 A1 | 12/2002 | Kornelsen |
| 2003/0113907 A1 | 6/2003 | Roberts |
| 2004/0031331 A1 * | 2/2004 | Blakley ............... A61M 15/009 73/862.52 |
| 2004/0206749 A1 | 10/2004 | Villa |
| 2010/0224255 A1 | 9/2010 | Mathies |
| 2010/0266449 A1 | 10/2010 | Wu et al. |
| 2014/0051159 A1 | 2/2014 | Bergstedt et al. |
| 2014/0106364 A1 * | 4/2014 | Desmond .......... B01L 3/502715 435/6.12 |
| 2014/0186846 A1 | 7/2014 | Tanaka et al. |
| 2016/0158760 A1 | 6/2016 | Wright |
| 2016/0310948 A1 | 10/2016 | Nowakowski et al. |

FOREIGN PATENT DOCUMENTS

| | | | |
|---|---|---|---|
| CN | 103389171 A | * | 11/2013 |
| CN | 105612001 A | | 5/2016 |
| EP | 1418243 A2 | | 5/2004 |
| EP | 3234594 A0 | | 10/2017 |
| WO | WO-2005058500 | | 6/2005 |
| WO | WO-2008117210 A1 | * | 10/2008 |
| WO | WO-2018194635 A1 | * | 10/2018 |

OTHER PUBLICATIONS

English Translation of CN 103318917A (Year: 2013).*
Coelho, B et al., Digital Microfluidics for Nucleic Acid Amplification, Jun. 25, 2017, Sensors 2017, 17.
Lietaer, N. et al., Wafer-level Packaged Mems Switch with TSV, Jun. 8, 2014.
Pardy, T. et al., Development of Temperature Control Solutions for Non-instrumented Nucleic Acid Amplification Tests (NINAAT), 2017, Micromachines 2017, 8, 180.

* cited by examiner

*Primary Examiner* — Stephanie K Mummert
*Assistant Examiner* — Olayinka A Oyeyemi
(74) *Attorney, Agent, or Firm* — Foley & Lardner LLP

(57) ABSTRACT

A fluid thermal processing device may include a substrate, a platform projecting from the substrate, a fluid heating element supported by the platform, a temperature sensing element, distinct from the fluid heating element, supported by the platform and an enclosure supported by and cooperating with the substrate to form a fluid chamber about the platform. The fluid chamber forms a volume of uniform thickness conforming to and about the platform.

20 Claims, 3 Drawing Sheets

FLUID THERMAL PROCESSING

CROSS-REFERENCE TO RELATED APPLICATIONS

This Utility Patent Application is a U.S. National Stage filing under 35 U.S.C. § 371 of PCT/US2018/054265, filed Oct. 3, 2018, which claims priority to PCT/2018/013848, filed Jan. 16, 2018, each of which are incorporated by reference herein.

BACKGROUND

Various processes may involve the heating of a fluid. One example of such a process is nucleic acid amplification wherein a fluid, such as a sample reagent mixture, is thermal cycled. During such thermal cycling, the sample reagent mixture is heated and cooled multiple times as part of amplifying a targeted nucleic acid, if present.

Figure 1:
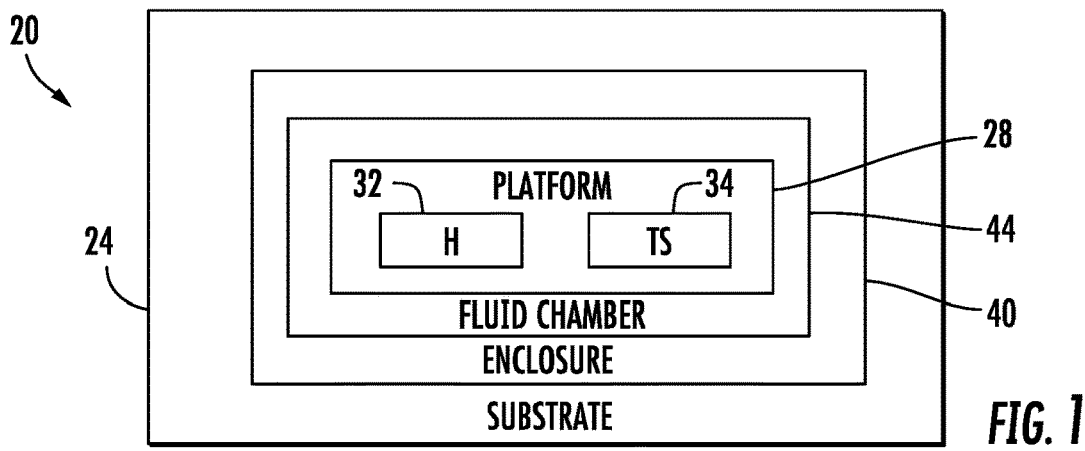
FIG. 1 is a block diagram illustrating portions of an example fluid thermal processing device.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Many fluid thermal processing systems currently used to heat fluids are bulky, complex and expensive. Such systems are often not portable and are difficult to use. Moreover, such current systems may lack precise control over the temperature to which the fluid is heated (and/or cooled) or may involve long periods of time to carry out multiple heating and cooling cycles.

Disclosed herein are example fluid thermal processing devices, fluid thermal processing methods and fluid thermal processing sticks that addresses many of the above described shortcomings. The disclosed example fluid thermal processing devices, fluid thermal processing methods and fluid thermal processing sticks facilitate more efficient and faster thermal processing of fluids. In particular, the disclosed example fluid thermal processing devices, fluid thermal processing methods and fluid thermal processing sticks have a geometry that provides efficient transfer and distribution of generated heat to and from the fluid being thermally processed. At the same time, the example devices, methods and sticks provide a compact package that offers precise control over the temperature of the fluid being thermally processed. As a result, the disclosed thermal processing devices, fluid thermal processing methods and fluid thermal processing sticks are well-suited for thermally processing fluids, such as in polymerase chain reaction (PCR) protocols and other thermal processing protocols.

The example fluid thermal processing devices, fluid thermal processing methods and fluid thermal processing sticks provide a high surface-to-volume ratio platform, providing high thermal transfer over a larger area with more fluid in direct or close contact with a heat source to deliver better and faster thermal control. As a result, such example devices, methods and sticks may provide precise temperature control and/or rapid cycling between temperatures in a small fluid volume, returning faster results. Such precise control over the temperature facilitates thermal cycling of lower fluid volumes, reducing reagent costs as well as reducing the material cost of the device or stick. The example platform further provides the opportunity for more sensors per platform surface area for enhanced temperature detection. In addition, the example fluid thermal processing devices, fluid thermal processing methods and fluid thermal processing sticks facilitate thermal cycling in a mobile form factor, permitting tests to be taken out of the lab and into the field.

Disclosed herein is an example fluid thermal processing device for carrying out a fluid thermal processing method. The device may include a substrate, a platform projecting from the substrate, a fluid heating element supported by the platform, a temperature sensing element, distinct from the fluid heating element, supported by the platform and an enclosure supported by and cooperating with the substrate to form a fluid chamber about the platform. The fluid chamber forms a volume of uniform thickness conforming to and about the platform. Because the volume has a uniform thickness conforming to and about the platform, heat generated by or on the platform, and conducted by the platform to the surrounding fluid more uniformly heats the fluid within the volume. As a result, the temperature of the fluid is more rapidly and uniformly elevated. Likewise, the temperature the fluid may be more rapidly and uniformly cooled. Thus, thermal cycling is faster and efficient.

For purposes of this disclosure, the thickness of the gap or volume conforms to and about the platform by enveloping or mirroring the shape of the platform. In other words, each portion of interior surface of the enclosure is parallel to the directly opposite portion of the exterior surface of the platform along substantially the entire exterior surface of the platform that is exposed to the volume. The term "uniform" with respect to the thickness of the volume or gap that conforms to and about a platform means a substantially equal spacing between a first portion of the exterior surface of the platform and a second portion of interior surface of the enclosure that is directly opposite the first portion, the second portion existing at a point of a line perpendicularly extending from the first portion. A "substantially equal spacing" means the same spacing plus/minus 10%. Such "uniformity" of the thickness of the gap the distance between opposing corners of the platform and the interior surface of the enclosure.

In some implementations, both the platform and the interior shape of the volume may be identical in shape. In other implementations, corners of the platform and/or interior corners of the chamber may be rounded. In some implementations, the interior corners of the chamber may be filled or formed by fillets. In some implementations, the exterior corners of the platform may be beveled. In some implementations, the platform may be rectangular or have a rectangular cross-section. In other implementations, the platform may have other shapes or other cross-sectional shapes.

In some implementations, the uniform thickness of the volume or gap that conforms to and about the platform is no greater than 200 μm. This spacing may facilitate uniform heating of the fluid within the volume or gap to temperatures that may be utilized as part of a thermal cycling process by heating elements, such as electrical resistors that may be supported upon the platform. For example, the second may facilitate uniform heating of a fluid, such as a sample reagent mixture for which a targeted nucleic acid is being detected, to a temperature of at least 90° C. for thermal cycling. In some implementations, depending upon the heating elements, the uniform thickness may be greater than 200 μm.

In some implementations, the platform is formed from at least one material having a high thermal diffusivity. Thermal diffusivity may be measured using a transient hotwire liquid thermal conductivity meter (the THW method) via ASTM D7896-14—Standard Test Method for Thermal conductivity, thermal diffusivity and volumetric heat capacity of engine coolant and related fluids by transient hotwire liquid thermal conductivity method. For purposes of this disclosure, all values pertaining to thermal dish diffusivity are taken pursuant to the above THW method. In one implementation, the platform is formed from material having a thermal diffusivity of at least 0.5 $cm^2/s$. In another implementation, the platform is formed from material having a thermal diffusivity of at least 0.1 $cm^2/s$. In some implementations, the platform is formed from a dielectric or semi-conductive material having a much higher thermal diffusivity, such as at least 1 $cm^2/s$. For example, in some implementations, the platform is formed from at least one silicon-based material, such as silicon, silicon carbide, silicon nitride and the like. The high thermal diffusivity of the material forming the platform more evenly or uniformly conducts or transfers heat generated on or within the platform to the surrounding fluid.

Because the platform is formed from a dielectric or semi-conductive material, the platform is well-suited for supporting electronic components or circuitry utilized to control the heating element provided and the temperature sensor on the platform. In some implementations, the dielectric or semi-conductive material of the platform facilitates the support of electronic circuitry utilized to control the heating element or the temperature sensor. In some implementations where the platform is formed from a semi-conductive material such as silicon, transistors or other electronic componentry may be directly formed in the platform, reducing the cost, complexity and size of the thermal processing device.

In some implementations, the platform has a width with a length of at least 10 times the width. The platform, formed as a "sliver", has a long length providing a large surface area for conducting heat to and away from the surrounding fluid. In one implementation, the temperature sensor may extend at least 50% of the length. In one implementation, the heating element may also extend along at least 50% of the length. In some implementations, the heating element and/or the temperature sensing element maybe one of a plurality of such heating elements or a plurality of such temperature sensing elements, respectively to provide distinct heating zones and temperature measurement regions along the length of the platform. In some implementations, the temperature sensor and/or the heating element may extend at least 50% of the length. In some implementations, the temperature sensor and/or the heating element may extend at least 75% of the length.

Disclosed herein is an example fluid thermal processing method. The method may involve supporting a fluid heating element on a platform that projects from a substrate, supplying a fluid into a volume about the platform, the volume having a substantially uniform thickness conforming to and extending about the platform, heating the fluid within the fluid chamber about the platform with a heating element supported by the platform and sensing a temperature of the fluid about the platform with a temperature sensing element distinct from the heating element and supported by the platform.

Disclosed herein is an example fluid thermal processing stick. The fluid thermal processing stick provides a compact and portable device for thermal processing fluid. The example fluid thermal processing stick may include a first end supporting an electrical interconnect that is to be operatively coupled to a controller and a second end forming a fluid interactor. The fluid interactor may comprise a platform having a width and a length, wherein the length is at least 10 times the width. The platform may support a heating element under control of the controller. The platform may further support a temperature sensing element distinct from the heating element to output temperature measurements to the controller. The example fluid thermal processing stick may include an enclosure supported by and cooperating with the substrate to form a fluid chamber about the platform. The fluid chamber forms a volume of uniform thickness conforming to and about the platform.

FIG. 1 is a block diagram of portions of an example fluid thermal processing device 20. Fluid thermal processing device 20 has a geometry that provides efficient transfer and distribution of generated heat to and from the fluid being thermally processed. Fluid thermal processing device 20 offers precise control over the temperature of the fluid being thermally processed such that it is well-suited for thermally processing fluids, such as in polymerase chain reaction (PCR) protocols and other thermal processing protocols. Fluid thermal processing device 20 comprises substrate 24, platform 28, fluid heating element 32, temperature sensing element 34, an enclosure 40.

Substrate 24 comprises at least one layer of material forming a base that supports platform 28. Substrate 24 may be formed from a variety of materials including, but not limited to, polymers, semiconductors, ceramics, glass and the like. In one implementation, substrate 24 is formed from silicon. In the example illustrated, in one implementation, substrate 24 underlies platform 28. In yet other implementations, platform 28 hangs from or is suspended from substrate 24. In some implementations, substrate 24 may comprise a printed circuit board. For example, in some implementations, substrate 24 may comprise a glass reinforced epoxy board, such as an FR4 board, upon which electrically conductive traces and electronic componentry are formed or supported.

Platform 28 comprises a structure that projects from substrate 24 and that supports heating element 32 and temperature sensing element 34. In one implementation, platform 28 comprises an elongate rectangular step or bar. In yet other implementations, platform 28 may have other shapes. In one implementation, platform 28 is formed from a material or a group of materials or a set of layers having a high thermal diffusivity so as to diffuse heat generated by heat element 32 to the fluid in contact with platform 28 such as the outer surface of platform 28 including its top/bottom and sides. In one implementation, platform 28 is formed from material having a thermal diffusivity of at least 0.5 cm²/s. In another implementation, the platform 28 is formed from material having a thermal diffusivity of at least 0.1 cm²/s.

In some implementations, platform 28 is formed from a dielectric or semi-conductive material having a high degree of thermal diffusivity, such as at least 8 cm²/s. For example, in some implementations, the platform 28 is formed from at least one silicon-based material, such as silicon, silicon carbide, silicon nitride and the like. The high thermal diffusivity of the material forming the platform 28 more evenly or uniformly conducts or transfers heat generated on or within the platform to the surrounding fluid.

Because platform 28 is formed from a dielectric or semi-conductive material, the platform is well-suited for supporting electronic components or circuitry utilized to control heating element(s) provided and the temperature sensor(s) on the platform. In some implementations, the dielectric or semi-conductive material of the platform 28 facilitates the support of electronic circuitry utilized to control the heating element or the temperature sensor. In some implementations where the platform is formed from a semi-conductive material such as silicon, transistors or other electronic componentry may be directly formed in the platform, reducing the cost, complexity and size of the thermal processing device. In some implementations, the platform 28 has a width and a length of at least 10 times the width. The platform, formed as a "sliver", has a long length providing a large surface area for conducting heat to and away from the surrounding fluid.

Fluid heating element 32 comprises an element that outputs heat. For example, in one implementation, fluid heating element 32 may comprise an electrical resistor that outputs heat in response to being supplied with electrical current. In one implementation, fluid heating element 32 is formed on an exterior surface of platform 28. In another implementation, fluid heating element 32 is embedded within the layer or layers forming platform 28. In one implementation, fluid heating element 32 extends along at least 50% of a length of platform 28. In one implementation, fluid heating element 32 is one of a plurality of fluid heating elements 32 disposed along the length of platform 28. For example, in one implementation, the plurality of fluid heating elements 28 may collectively extend along at least 50% of the length of platform 28.

Temperature sensing element 34 comprises an element that outputs signals indicating a temperature of the fluid within the fluid chamber. In one implementation, the temperature sensing element 34 may directly sense the temperature the fluid. In yet another implementation, the temperature sensing element 34 may indirectly sense the temperature of the fluid by sensing the temperature of a physical component or structure, the temperature of which is correlated to the temperature of the fluid. Temperature sensing element 34 is independent of and distinct from heating element 32. As a result, heating element 32 and temperature sensing element 34 may be independently located along platform 28, may be provided lower-cost distinct elements and may be independently controlled and monitored. Distinct heating and sensing elements enable more precise thermal control than a single element (e.g. a thermal sense resistor) can afford. In one implementation, temperature sensing element 34 may comprise thermal temperature sense resistors In one implementation, the temperature sensor 34 may extend at least 50% of the length of platform 28. In some implementations, the temperature sensing element 34 may be one of a plurality of such temperature sensing elements, to provide distinct temperature measurement regions along the length of the platform 28. In one implementation, multiple temperature sensing elements 34 collectively extend at least 50% of the length of platform 28. In other implementations, the multiple temperature sensing elements may collectively extend at least 75% of the length of the platform 28.

Enclosure 40 comprises a structure supported by and cooperating with substrate 24 to form a fluid chamber 44 having a volume of uniform thickness that conforms to and about platform 28. This uniform thickness conforms to platform 28 in at least first and second dimensions, wherein fluid may exit and/or enter the fluid chamber in the third dimension. In some implementations, this uniform thickness may conform to platform 28 in all three dimensions, but wherein an exception to the uniformity exists where fluid input and/or output ports communicate with the fluid chamber.

In one implementation, the fluid chamber has a ceiling formed by enclosure 40 and a floor formed by substrate 24. In one implementation, interior sides of the fluid chamber are provided by sidewalls of enclosure 40. In another implementation, interior sides of the fluid chamber are formed by sidewalls of substrate 24, where enclosure 40 is a dome or lid. In yet other implementations, some of the sidewalls that form fluid chamber may be provided by substrate 24 while other of the sidewalls forming fluid chamber 44 are provided by enclosure 40.

Because the volume of fluid chamber 44 has a uniform thickness conforming to and about the platform 28, heat generated by or on the platform 28, and conducted by the platform 28 to the surrounding fluid more uniformly heats the fluid within the volume. As a result, the temperature of the fluid is more rapidly and uniformly elevated. Likewise, the temperature the fluid may be more rapidly and uniformly cooled. Thus, thermal cycling is faster and efficient.

In some implementations, the uniform thickness of the volume or gap that conforms to and about the platform is no greater than 200 μm. This spacing may facilitate uniform heating of the fluid within the volume or gap to temperatures that may be utilized as part of a thermal cycling process by heating elements, such as electrical resistors that may be supported upon the platform. For example, the second may facilitate uniform heating of a fluid, such as a sample reagent mixture for which a targeted nucleic acid is being detected, to a temperature of at least 90° C. for thermal cycling. In some implementations, depending upon the heating elements, the uniform thickness may be greater than 200 μm.

In one implementation, enclosure 40 is integrally formed as a single unitary body. In yet other implementations, enclosure 40 is formed from multiple sections, segments or panels bonded, welded, fastened or otherwise joined to one another. In one implementation, enclosure 40 is formed from the same material as that of substrate 24. In other implementations, enclosure 40 may be formed from a material distinct from that of substrate 24. In some implementations, enclosure 40 comprises side wall portions and a lid that forms an interior surface of the fluid chamber opposite substrate 24. In such an implementation, the lid portion of enclosure 40 may have a thickness of at least 50 micrometers, and in some implementations, up to 1000 μm, where such a thickness reduces thermal cycling time by facilitating faster cooling/convective heat transfer.

Figure 2:
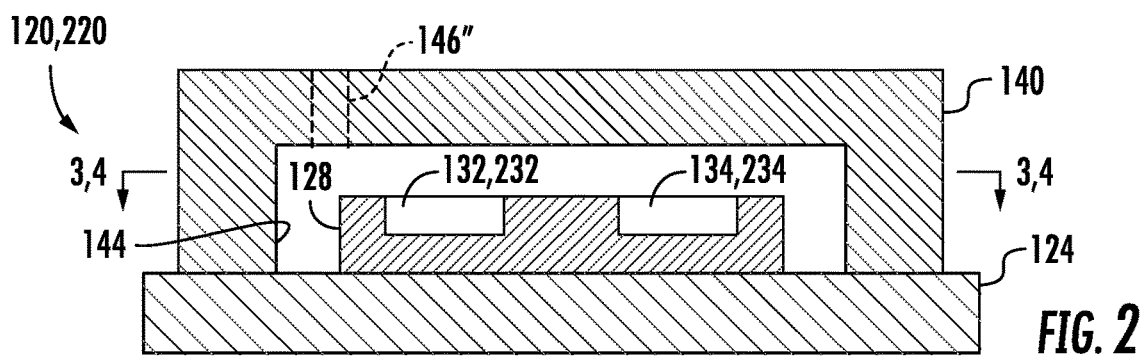
FIG. 2 is a cross-sectional view illustrating portions of an example fluid thermal processing device.
Figure 3:
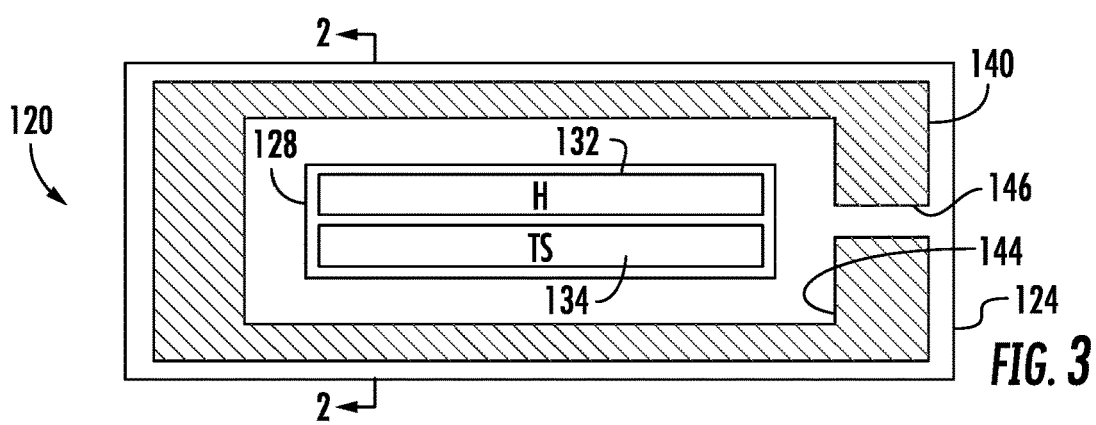
FIG. 3 is a sectional view of the example fluid thermal processing device of FIG. 2 taken along line 3-3.

FIGS. 2 and 3 illustrate portions of an example fluid thermal processing device 120. FIG. 2 is a sectional view of device 120 taken along line 2-2 of FIG. 3. FIG. 3 is a sectional view of device 120 taken along line 3-3 of FIG. 2. As with fluid thermal processing device 20, fluid thermal processing device 120 provides a high surface-to-volume ratio platform, providing high thermal transfer over a larger area with more fluid in direct or close contact with a heat source to deliver better and faster thermal control. As a result, fluid thermal processing device 120 may provide precise temperature control and/or rapid cycling between temperatures in a small fluid volume, returning faster results. Such precise control over the temperature facilitates thermal cycling of lower fluid volumes, reducing reagent costs as well as reducing the material cost of the device or stick. The example platform of device 120 further provides the opportunity for more sensors per platform surface area for enhanced temperature detection. In addition, the example fluid thermal processing device 120 may facilitate thermal cycling in a mobile form factor, permitting tests to be taken out of the lab and into the field. The example fluid thermal processing device 120 shown in FIGS. 2 and 3 comprises substrate 124, platform 128, fluid heating element 132, temperature sensing element 134, and enclosure 140.

Substrate 124 comprises at least one layer of material forming a base that supports platform 128. Substrate 124 may be formed from a variety of materials including, not limited to, polymers, semiconductors, ceramics, glass and the like. In one implementation, substrate 124 is formed from silicon. In some implementations, substrate 124 may comprise a printed circuit board. For example, in some implementations, substrate 124 may comprise a glass reinforced epoxy board, such as an FR4 board, upon which electrically conductive traces and electronic componentry are formed or supported.

In the example illustrated, substrate 124 underlies platform 128. In yet other implementations, platform 124 hangs from or suspended from substrate 124.

Platform 128 comprises a structure that projects from substrate 124 and that supports heating element 132 and temperature sensing element 134. In the example illustrated, platform 124 comprises an elongated rectangular step or bar. In yet other implementations, platform 124 may have other shapes. In the example illustrated, platform 124 is formed from a material or a group of materials or a set of layers having a high thermal diffusivity so as to diffuse heat generated by heat element 132 to the fluid in contact with platform 128 such as the outer surface of platform 124 including its top/bottom and sides. In one implementation, platform 128 is formed from material having a thermal diffusivity of at least 0.5 cm$^2$/s. In another implementation, the platform 128 is formed from material having a thermal diffusivity of at least 0.1 cm$^2$/s.

In some implementations, platform 128 is formed from a dielectric or semi-conductive material having a high degree of thermal diffusivity, such as at least 1 cm$^2$/s. For example, in some implementations, the platform 128 is formed from at least one silicon-based material, such as silicon, silicon carbide, silicon nitride and the like. The high thermal diffusivity of the material forming the platform 128 more evenly or uniformly conducts or transfers heat generated on or within the platform to the surrounding fluid.

Because platform 128 is formed from a dielectric or semi-conductive material, the platform is well-suited for supporting electronic components or circuitry utilized to control heating element provided and the temperature sensor on the platform. In some implementations, the dielectric or semi-conductive material of the platform 128 facilitates the support of electronic circuitry utilized to control the heating element or the temperature sensor. In some implementations where the platform is formed from a semi-conductive material such as silicon, transistors or other electronic componentry may be directly formed in the platform, reducing the cost, complexity and size of the thermal processing device. In one implementation, the platform 128 has a width and a length of at least 10 times the width. The platform 128, formed as a "sliver", has a long length providing a large surface area for conducting heat to and away from the surrounding fluid.

Fluid heating element 132 comprises an element that outputs heat. For example, in one implementation, fluid heating element 132 may comprise an electrical resistor that outputs heat in response to being supplied with electrical current. In one implementation, fluid heating element 132 is formed on an exterior surface of platform 128. In another implementation, fluid heating element 132 is embedded within the layer or layers forming platform 128. In one implementation, fluid heating element 132 extends along at least 50% of a length of platform 128. In one implementation, fluid heating element 132 extend along at least 75% of the length of platform 128.

Temperature sensing element 134 comprises an element that outputs signals indicating a temperature of the fluid within the fluid chamber. In one implementation, the temperature sensing element 134 may directly sense the temperature the fluid. In yet another implementation, the temperature sensing element 34 may indirectly sense the temperature of the fluid by sensing the temperature of a physical component or structure, the temperature of which is correlated to the temperature of the fluid. Temperature sensing element 34 is independent of and distinct from heating element 134. As a result, heating element 132 and temperature sensing element 134 may be independently located along platform 128, may be provided lower-cost distinct elements and may be independently controlled and monitored. In one implementation, temperature sensing element 134 may comprise thermal temperature sense resistors. In one implementation, the temperature sensor 134 may extend at least 50% of the length of platform 128. In one implementation, a sensing element 134 may extend at least 75% of the length of platform 128.

Enclosure 140 comprises a structure extending from substrate 124 at least partially around, over and about platform 128 to form a fluid chamber 144 having a volume of uniform thickness that conforms to and about platform 128. This uniform thickness conforms to platform 128 in at least first and second dimensions, wherein fluid may exit and/or enter the fluid chamber in the third dimension. In the example illustrated, this uniform thickness may conform to platform 128 in all three dimensions, but wherein an exception to the uniformity exists for an input/output port 146 that extends through enclosure 40 and communicates with the interior of fluid chamber 144. Although port 146 is illustrated extending through a short side of enclosure 140, in other implementations, port 146 may alternatively extend into communication with chamber 144 at other locations. For example, as indicated by broken lines, in other implementations, enclosure 140 may comprise a port 146' through a long side of enclosure 140 and/or a port 146" through a lid or ceiling portion of enclosure 144. In some implementations, device 120 may include multiple distinct ports.

Because the volume of fluid chamber 144 has a uniform thickness conforming to and about the platform 128, heat generated by or on the platform 128, and conducted by the platform 128 to the surrounding fluid more uniformly heats the fluid within the volume. As a result, the temperature of the fluid is more rapidly and uniformly elevated. Likewise, the temperature the fluid may be more rapidly and uniformly cooled. Thus, thermal cycling is faster and efficient.

In some implementations, the uniform thickness of the volume or gap that conforms to and about the platform is no greater than 200 µm. This spacing may facilitate uniform heating of the fluid within the volume or gap to temperatures that may be utilized as part of a thermal cycling process by heating elements, such as electrical resistors that may be supported upon the platform. For example, the uniform thickness of the gap may facilitate uniform heating of a fluid, such as a sample reagent mixture for which a targeted nucleic acid is being detected, to a temperature of at least 90° C. for thermal cycling. In some implementations, depending upon the heating elements, the uniform thickness may be greater than 200 µm.

In one implementation, enclosure 140 is integrally formed as a single unitary body. In yet other implementations, enclosure 140 is formed from multiple sections, segments or panels bonded, welded, fastened or otherwise joined to one another. In one implementation, enclosure 140 is formed from the same material as that of substrate 124. In other implementations, enclosure 140 may be formed from a material distinct from that of substrate 124. In some implementations, enclosure 140 comprises side wall portions and a lid that forms an interior surface of the fluid chamber opposite substrate 124. In such an implementation, the lid portion of enclosure 140 may have a thickness of at least 50 micrometers, and in some implementations, up to 1000 µm, where such a thickness reduces thermal cycling time by facilitating faster cooling/convective heat transfer.

Figure 4:
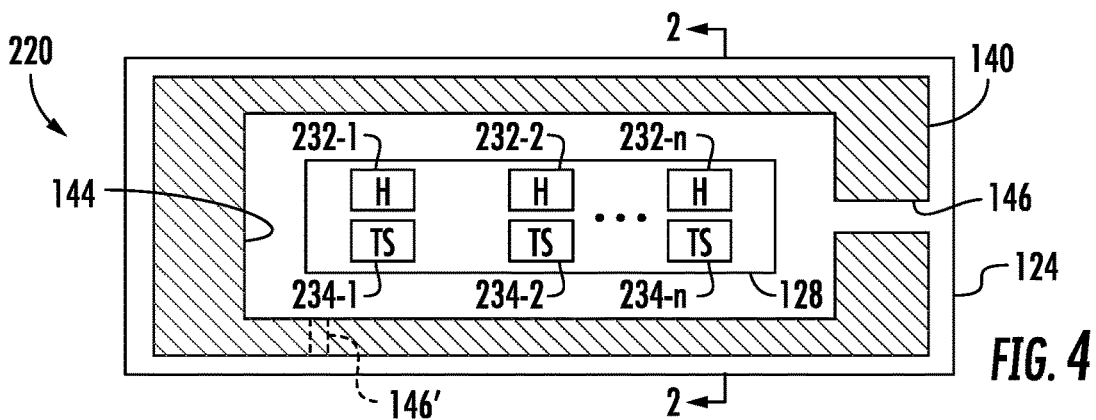
FIG. 4 is a sectional view of an example fluid thermal processing device taken along line 3-3 of FIG. 2.

FIGS. 2 and 4 illustrate portions of an example fluid thermal processing device 220. FIG. 2 is a sectional view of the device of FIG. 4 taken along line 2-2 of FIG. 4. FIG. 4 is a sectional view of the device of FIG. 2 taken along line 4-4 of FIG. 2. Fluid thermal processing device 220 is similar to fluid thermal processing device 120 described above except that fluid thermal processing device 220 comprises multiple distinct heating elements 232-1, 232-2, . . . 232-n (collectively referred to as elements 232) and multiple distinct temperature sensing elements 234-1, 234-2, . . . 234-n (collectively referred to as elements 234). Those remaining components of fluid thermal processing device 220 which correspond to components of fluid thermal processing device 120 are numbered similarly.

Heating elements 232 are each similar to heating element 132 described above. Heating elements 232 are individually spaced along the length (the major dimension) of platform 128. Each of heating elements 232 is distinct in that it is independently controllable and actuatable. As a result, heating elements 232 may be differently actuated to provide multiple distinct heating zones or temperature zones within fluid chamber 144. In one implementation, heating elements 232 collectively span at least 50% of the length of platform 128. In other implementations, heating elements 232 collectively span at least 75% of the length of platform 128. The heat emitted by heating elements 232 is absorbed by platform 128 and substantially uniformly diffused to the fluid within fluid chamber 144. In one implementation, heating elements 232 may be separated from the bulk material of platform 128 by a thin passivation layer; however, the thin passivation layer does not interfere with or interrupt the transfer of heat from the heating elements 232 to the bulk material of platform 128.

Temperature sensing elements 234 are each similar to temperature sensing elements 134 described above. Temperature sensing elements 234 are individually spaced along the length (the major dimension) of platform 128. Each of temperature sensing elements 234 is distinct in that is independently controllable and outputs distinct signals indicating the temperature of the fluid proximate to the individual temperature sensing element. Each of temperature sensing elements 234 is distinct from each of the heating element 232 for independent actuation and use. The multiple temperature sensing elements 234 facilitate the detection of distinct temperatures or temperature zones or regions along platform 128 and along the length of fluid chamber 144.

Although FIG. 4 illustrates a temperature sensing element 234 for each of heater elements 232, in other implementations, the number of heating elements 232 may be greater than the number of temperature sensing elements 234, or vice versa. Although heating elements 232 and temperature sensing elements 234 are illustrated as being insubstantial alignment with one another along the length of platform 128, in other implementations, heating elements 232 and temperature sensing elements 234 may be locationally offset or staggered relative to one another along the length of platform 128.

Figure 5:
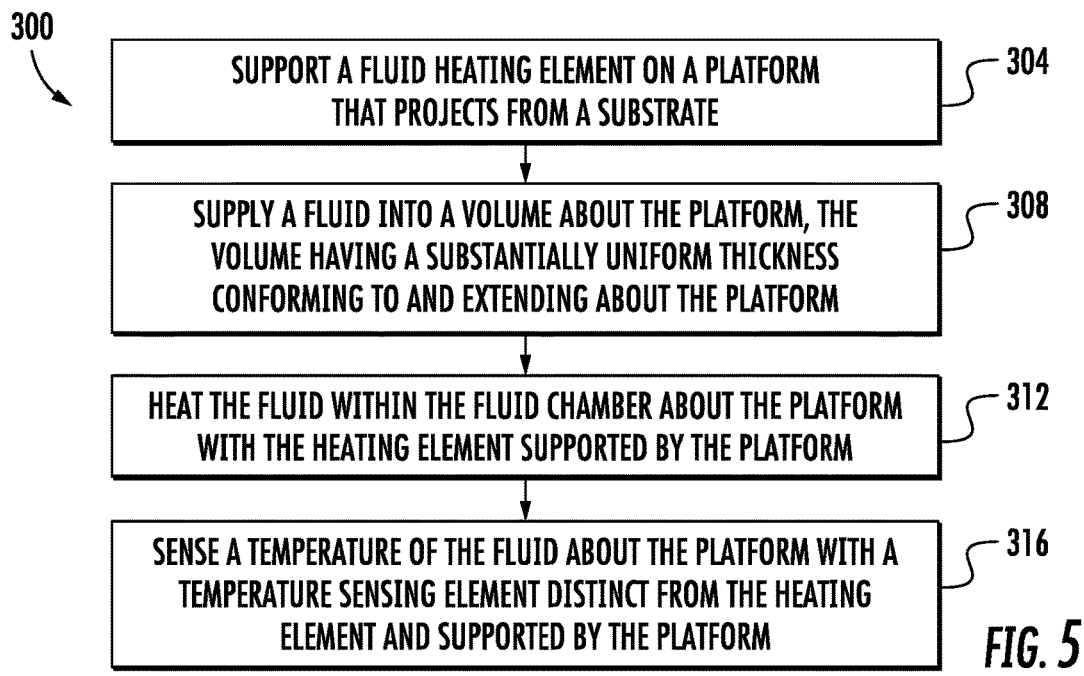
FIG. 5 is a flow diagram of an example fluid thermal processing method.

FIG. 5 is a flow diagram of an example fluid thermal processing method 300. Fluid thermal processing method 300 facilitates rapid heating and cooling of a fluid within a fluid chamber. In some implementations, fluid thermal processing method facilitates rapid thermal cycling of a fluid. Although method 300 is described in the context of being carried out by fluid thermal processing device 220, it should be appreciated that fluid thermal processing method 300 may likewise be carried out with fluid thermal processing device 20, fluid thermal processing device 120 or other similar fluid thermal processing devices.

As indicated by block 304, a fluid heating element, such as fluid one of heating element 32, is supported on a platform comes such as platform 28, that projects from a substrate, such as substrate 24. As indicated by block 308, a fluid is supplied into a volume, such as a volume of chamber 144, that extends about the platform. The volume has a substantially uniform thickness conforming to and extending about the platform.

As indicated by block 312, the fluid within the fluid chamber and about the platform is heated with at least one of the heating elements supported by the platform. As indicated by block 316, a temperature of the fluid about the platform is sensed with a temperature sensing element, such as at least one of temperature sensing elements 232, supported by the platform and distinct from the heating element.

Thermal processing method 300 is well suited for carrying out nucleic acid amplification testing (NAT or NAAT). NAT is a diagnostic method to test for detecting genetic materials to ascertain various states of health or disease. NAT is especially effective for detecting infectious agents in clinical samples and for applications in food safety, forensics, veterinary medicine, agriculture and the environment. DNA or RNA in raw samples is often at too low of a low concentration to be detectable. NAT may generate millions to billions of copies of specific sequences of DNA or RNA starting from as little as one original copy, enough to be detectable via optical or electrical mechanisms.

NAT generally involves one or more enzymes and associated support chemistry, such as a master mix, wherein the solution of the sample (DNA/RNA template) and support chemistry are processed using one or more heating modalities such as isothermal or thermal cycling as defined by the enzymes and support chemistry (master mix). The use of the processing method 300 as well as any of fluid thermal processing devices 20, 120, 220 described above (or the subsequently described thermal processing devices) provide faster heating and precise thermal control in a microliter scale reaction volumes. Such faster heating and enhanced thermal control, achieved by heating the fluid within the conformal volume about the platform and the use of distinct heating and temperature sensing elements, may facilitate faster copying or duplication of DNA/RNA sequences to achieve faster NAT.

One example NAT is polymer chain reaction (PCR) and its permutations. In one implementation in which method 300 and thermal processing devices 20, 120, 220 are used as part of a PCR, the solution composed of the RNA/DNA sample and the support chemistry/master mix (often including a DNA polymerase, such as Taq polymerase) is thermal cycled within the conformal volume or chamber about the platform between multiple different temperatures to achieve amplification. In one implementation, the solution undergoes 20 to 40 repeated temperature changes, called cycles, with each cycle including two or three discrete temperature steps. Such thermal cycling is achieved using the independent heating elements and temperature sensing elements supported by the platform. The cycling is sometimes preceded by a single temperature step at a very high temperature (greater than 90° C.) and is further followed by a hold at the end for final product extension or storage. The exact temperatures and length of the different cycles may vary depending upon the particular enzyme used for DNA synthesis, the concentration of bivalent ions and deoxynucleotide triphosphates (dNTP) in the reaction and the melting temperature of the primers.

In one implementation, such a PCR process includes an initialization step, wherein the heating elements heat the solution to a temperature of 94 to 96° C. (as measured by the distinct temperature sensing elements), this temperature is maintained for 1 to 10 minutes. Following this initialization step, a denaturization step is carried out wherein the solution in the reaction chamber is heated to a temperature of between 94 and 98° C. for 20 to 30 seconds so as to cause DNA melting or denaturation. During such denaturization of the double-stranded DNA template, the hydrogen bonds between complementary bases are broken, yielding two single-stranded DNA molecules.

Following denaturization, annealing is carried out. During annealing, the temperature is lowered to a temperature of between 50-65° C. (as measured by the distinct temperature sensing elements) for 20 to 40 seconds so as to allow the annealing of the primers to each of the single-stranded DNA molecules. In one implementation, two primers are included in the reaction mixture, one for each of the two single-stranded compliments containing the target region. The efficiency of the PCR process may be dependent on precise control over the temperature of the solution during annealing. During annealing, the temperature of the solution may heated/passively cooled to a temperature low enough to allow for hybridization of the primer to the strand, but high enough for the hybridization to be specific such as the primer binds only to a perfect complementary part of the strand. If the temperature is too low, the primer may have an imperfect bond. If the temperature is too high, the primer may not bind at all. The annealing temperature is often between about 3 degrees and 5 degrees below the melting temperature of the primers used.

Following annealing, extension/elongation is carried out. During such a step, the solution is heated (or allowed to cool) to an activity temperature of the DNA polymerase. For example, the activity temperature of a solution containing a Taq (*Thermus Aquaticus*) polymerase is approximately 75 to 80° C. to a temperature of 72° C. During this step, the DNA polymerase synthesizes a new DNA strand complementary to the DNA template strand by adding free dNTPs from the reaction mixture that are complementary to the nucleic acid template. The precise time for elongation may depend on both the DNA polymerase used and the length of the DNA target region being amplified.

In yet other implementations, thermal processing method 300 and thermal processing devices 20, 120, 220 may be used as part of other NAT procedures. For example, thermal processing method and devices 20, 120, 220 may be well suited for use in isothermal processes such as Loop Mediated Isothermal Amplification (LAMP), recombination-polymerase amplification (RPA), Helicase-Dependent Amplification (HDA) and others. The common thread among such NAT and amplification methods is a benefit from precise thermal control, combined with evaporation control and a master mix finely tuned to the detection technique being employed.

Figure 6:
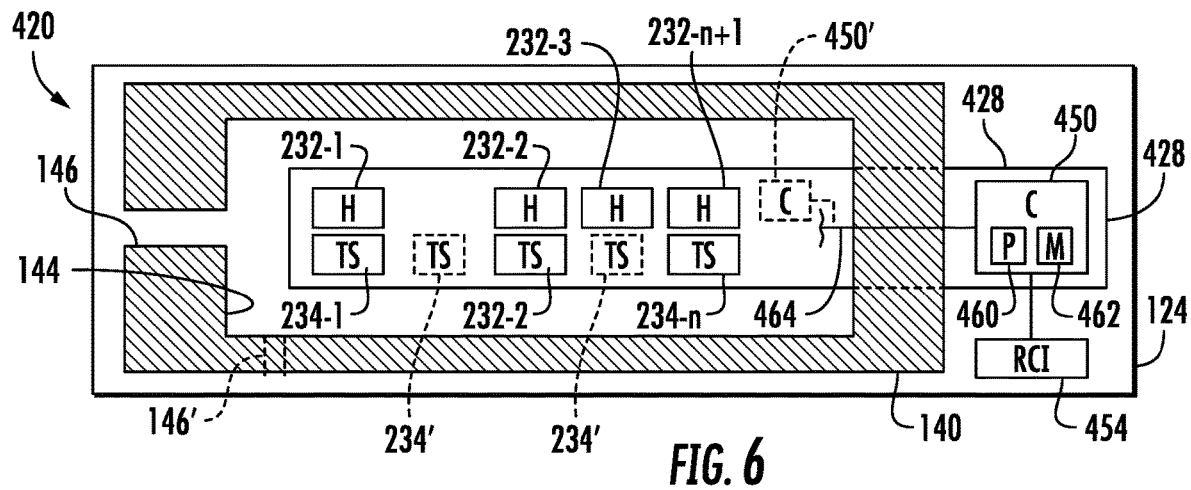
FIG. 6 is a sectional view of an example fluid thermal processing device.

FIG. 6 is a sectional view schematically illustrating portions of an example fluid thermal processing device 420. Fluid thermal processing device 420 is similar to fluid thermal processing device 220 except that fluid thermal processing device 420 comprises platform 428 in place of platform 128 and additionally comprises controller 450 and communication interface 454. Those remaining components of fluid thermal processing device 420 which correspond to components of fluid thermal processing device 220 are numbered similarly.

Platform 428 is similar to platform 128 except that platform 428 projects from within enclosure 140, through enclosure 140 and beyond the exterior of enclosure 140 on substrate 124 and that platform 428 is specifically formed from a material capable of supporting the electronic circuitry, transistors and the like of controller 450. In one implementation, platform 428 is formed from a dielectric or semi-conductive material having a high thermal diffusivity. In one implementation, platform 428 is formed from a-based material, such as silicon, silicon carbide or silicon nitride. In one implementation, platform 428 is formed from a material that may be doped to form thin-film transistors that serve as part of controller 450.

Similar to platform 128, platform 428 supports fluid heating elements 232 and temperature sensing elements 234. In the example illustrated, fluid heating elements 232 and temperature sensing elements 234 are not provided with a one-to-one correspondence. In the example illustrated, platform 428 supports a larger number of fluid heating elements 232 than temperature sensing elements 234. In one implementation, the fluid heating elements 232 are nonuniformly spaced and distributed along the length of platform 428, providing additional heating allocations where additional heating may be beneficial during the thermal processing of the fluid within chamber 144. In yet other implementations, as shown by broken lines, platform 428 may support a larger number of temperature sensing elements 234 as compared to fluid heating elements 232. For example, additional temperature sensing elements 234' may be provided in regions along platform 428 where additional temperature sensing resolution may be beneficial for a particular thermal processing of fluid.

Controller 450 comprises electronics for controlling the operation of fluid heating elements 232 based at least in part upon fluid temperature determinations based upon signals from temperature sensors 234 controller 450 is embedded within or mounted upon platform 428. One implementation, portions of controller 450, such as thin-film resistors, are formed by doping portions of the material of platform 428. Controller 450 communicates with each of fluid heating element 232 and each of temperature sensing elements 234 across the electrically conductive wires or traces 464 extending from controller 450, through enclosure 144 and on top of or within platform 428 to fluid heating elements 232 and temperature sensing elements 234.

In the example illustrated, controller 450 comprises processing unit 460 and non-transitory-computer-readable medium or machine-readable medium 462. Processing unit 460 may be in the form of logic elements or logic components forming an integrated circuit, such as an application specific integrated circuit. In other implementations, processing unit 460 may follow instructions contained in memory 462. Processing unit 460, following instructions contained in memory 462, retrieves or otherwise receives signals from temperature sensors 234 and determines a temperature of the fluid about platform 428 within fluid chamber 144. Based upon the sensed and determined temperature of the fluid in the different regions of fluid chamber 144, processing unit 460, following instructions contained in memory 462, outputs control signals selectively actuating fluid heating elements 232. In one implementation, memory 462 contains instructions causing controller 452 execute thermal cycling of the fluid within the chamber 144.

As shown by broken lines, in some implementations, fluid thermal processing device 420 may additionally or alternatively comprise a controller 450'. Controller 450' may replace controller 450 (including each of the components illustrated and described above with respect to controller 450) or may include such components but supplementing controller 450. Controller 450' may be located within chamber 144, supported by platform 428. In some implementations, such as where substrate 124 comprises a printed circuit board, controller 450' may be supported within chamber 144 and directly supported by substrate 124.

Communication interface 454 comprises an interface by which a remote controller, such as a controller not supported by the substrate 124, may communicate with controller 450. In one implementation, the controller interface 454 may comprise electric conductive, signal transmitting pads. In yet other implementations, remote control interface 454 may comprise a series of electrically conductive pins or sockets for connection to corresponding sockets and pins of a cable connected to the communication interface. In yet other implementations, controller 450 may communicate with external or remote controllers in a wireless fashion. In still other implementations, communication interface 454 may be omitted or communication interface 454 may be provided in the absence of controller 450, wherein each of the fluid heating elements 232 and detail sensing elements 234 are controlled directly by a remote or external controller.

Figure 7:
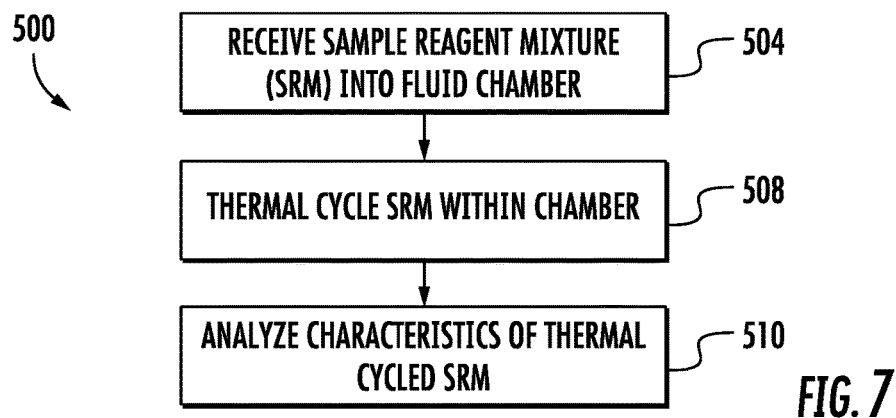
FIG. 7 is a flow diagram of an example fluid thermal processing method.

FIG. 7 is a flow diagram of an example fluid thermal processing method 500. Fluid thermal processing method 500 utilizes thermal cycling to analyze an analyte. In one implementation, such thermal cycling may be used to multiply any existing nucleic acid within the sample, amplifying the presence of such nucleic acid, to facilitate its detection.

In one implementation, such thermal cycling may be utilized as part of a polymerase chain reaction (PCR). Although method 500 is described in the context of being carried out by fluid thermal processing device 420, it should be appreciated that method 500 may likewise be carried out with any of the fluid thermal processing devices of the disclosure or other similar fluid thermal processing devices.

As indicated by block 504, a sample reagent mixture (SRM) is received by and into a fluid chamber, such as fluid chamber 144. The SRM may comprise a solution containing a fluid sample to which has been added reagents that facilitate nucleic acid multiplication or amplification.

As indicated by block 508, the fluid forming the SRM is thermal cycled within the chamber. In one implementation, the SRM is thermal cycled to carry out polymerase chain reaction. In other implementations, the SRM is thermal cycled to carry out other nucleic acid amplification protocols.

As indicated by block 510, characteristics of the fluid can be evaluated in real time or at the end of thermal processing. Such analysis may involve the detection or sensing of particular targeted analyte in the solution or the detection of the level of nucleic acid in the thermal cycled SRM.

Figure 8:
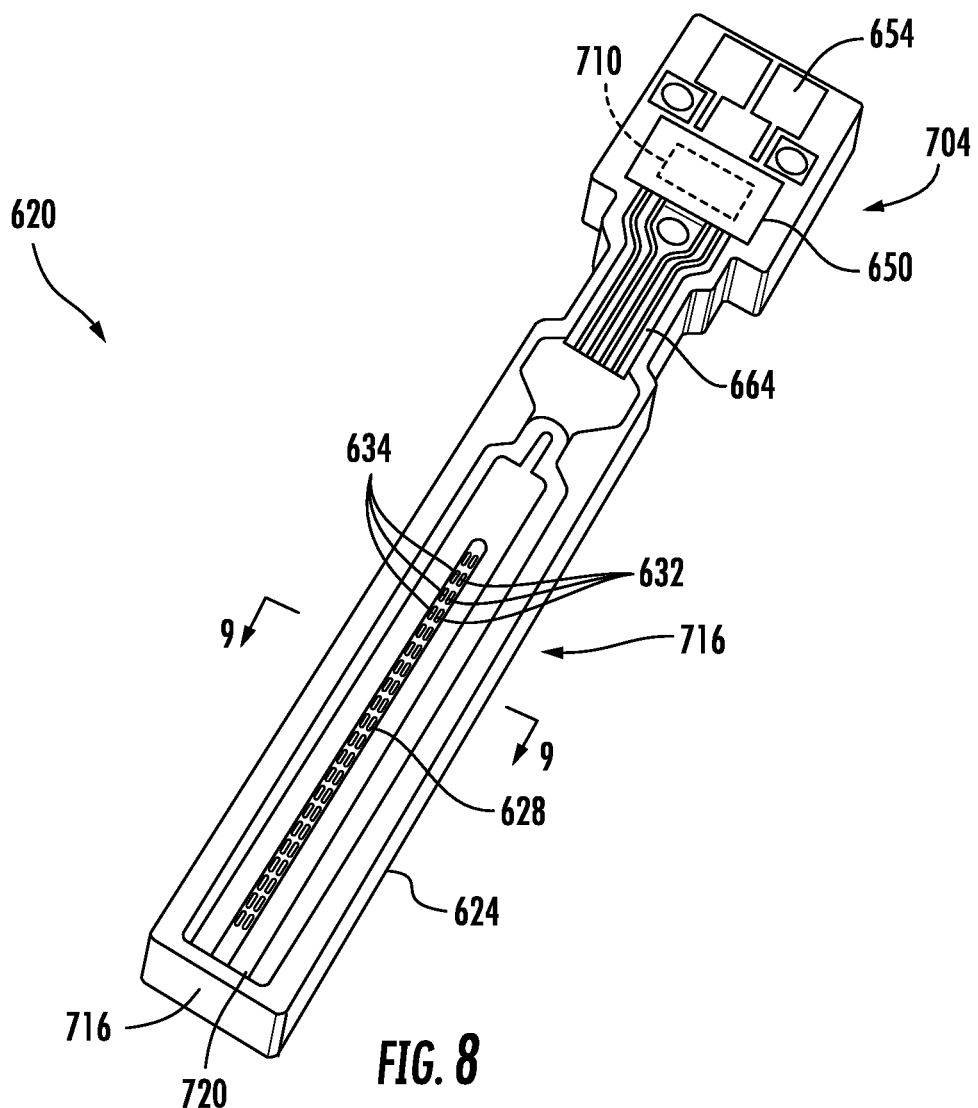
FIG. 8 is a perspective view of an example fluid thermal processing stick.
Figure 9:
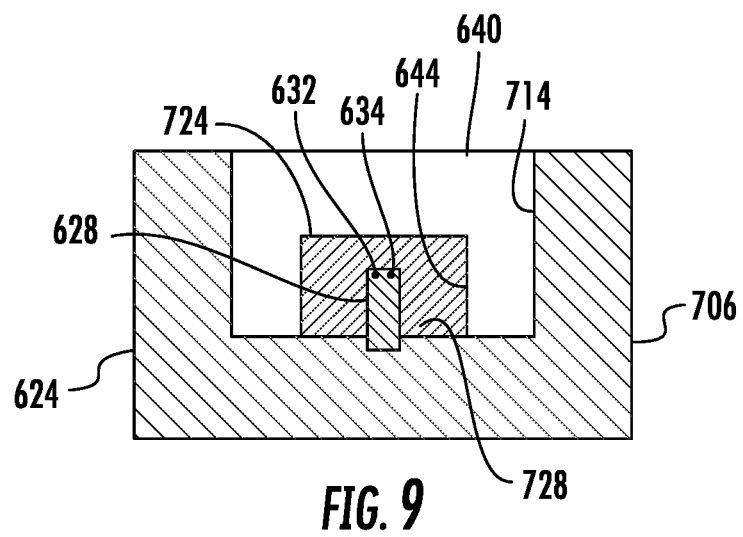
FIG. 9 is a cross-sectional view of the example stick of FIG. 8 taken along line 9-9.

FIGS. 8 and 9 illustrates portions of an example fluid thermal processing device in the form of a fluid thermal processing stick 620. FIG. 9 is a sectional view of the stick 620 of FIG. 8 taken along line 9-9. As with fluid thermal processing devices 20, 120, 220 and 420, thermal processing stick 620 provides a high surface-to-volume ratio platform, providing high thermal transfer over a larger area with more fluid in direct or close contact with a heat source to deliver better and faster thermal control. As a result, fluid thermal processing stick 620 may provide precise temperature control and/or rapid cycling between temperatures in a small fluid volume, returning faster results. Such precise control over the temperature facilitates thermal cycling of lower fluid volumes, reducing reagent costs as well as reducing the material cost of the device or stick. The example platform of stick 620 further provides the opportunity for more sensors per platform surface area for enhanced temperature detection. In addition, the example fluid thermal processing stick 620 may facilitate thermal cycling in a mobile form factor, permitting tests to be taken out of the lab and into the field. Stick 620 comprises substrate 624, platform 628, fluid heating elements 632, temperature sensing elements 634, enclosure 640, controller 650 and communication interface 454.

Substrate 624 comprises a body of material that supports remaining components of stick 620. In some implementations, substrate 624 may comprise a printed circuit board. For example, in some implementations, substrate 624 may comprise a glass reinforced epoxy board, such as an FR4 board, upon which electrically conductive traces and electronic componentry are formed or supported.

As shown by FIG. 9, substrate 624 has an upper body 704 and a lower body 706. Upper body 704 extends to one end of the recess, supporting controller 650 and communication interface 654. In one implementation, upper body 704 serves as a handle for stick 620.

Controller 650 includes circuitry, such as an application-specific integrated circuit, that controls fluid heating elements 632 and temperature sensing element 634. In one implementation, controller 650 may comprise hardware in the form of a processing unit that follows instructions contained in software supported by upper body 704 or communicated to controller 650 through communication interface 654. In some implementations, controller 650 may be omitted, wherein elements 632 and 634 are controlled by signals received through communication interface 654 from a remote controller or remote electronic device.

Communication interface 654 facilitates communication with controller 650. In one implementation, communication interface 654 facilitates a wired connection. For example, in one implementation, communication interface 654 may comprise an electrical interconnect or contact pad or pads. In one implementation, communication interface 654 may comprise a male or female port or plug for connection to a separate device, directly or through at least one cable or adapter.

In yet another implementation, communication interface 654 may facilitate wireless communication. For example, in one implementation, communication interface 654 may comprise a communication antenna serving as a one-way or two-way wireless transponder. In one implementation, communication interface 654 may comprise an active radio frequency tag. In yet another implementation, communication interface 654 may comprise a passive radio frequency tag. In still other implementations, communication interface 654 may communicate via Bluetooth or in other wireless communication manners.

In some implementations, communication interface 654 may be omitted such as where controller 650 carries out analysis and testing and directly indicates results on stick 620. For example, in one implementation, stick 620 may additionally comprise an indicator 710 (shown in broken lines) supported by upper body 704 and in communication with controller 650. In one implementation, the indicator 710 may comprise at least one light emitting temperature sense resistor which is illuminated by controller 650 based upon the testing results. In such an implementation, indicator 710 may also indicate a current status of the testing process or test being carried out.

Lower body 706 is recessed, forming a U-shaped channel 7144 receiving enclosure 640. Lower body 706 cooperates with enclosure 640 to form a fluid chamber 644. In the example illustrated, lower body 706 forms a floor of the formed chamber 644. In one implementation, lower body 706 is integrally formed as a singer unitary body. In other implementations, lower body 706 may be formed from multiple separate structures mounted, fuse, bonded, welded or fastened to one another. In one implementation, substrate 624 is formed materials such as polymers, ceramics, glass or silicon.

Platform 628 comprises at least one structure upon which fluid heating elements 632 and temperature sensing element 634 are provided or supported. In the example illustrated, platform 628 comprises an elongate bar, strip or sliver that supports the individual interaction elements and which further supports or encloses electrical wiring or electrical traces 664 for connection of controller 650 and/or communication interface 654 to the individual elements 632 and 634.

In one implementation, platform 628 is formed from a material or a group of materials having a height thermal diffusivity so as to diffuse heat generated by heat elements 632 to the fluid in contact with platform 628 such as the outer surface of platform 624 including its top/bottom and sides. In one implementation, platform 628 is formed from material having a thermal diffusivity of at least 0.5 cm$^2$/s. In another implementation, the platform 628 is formed from material having a thermal diffusivity of at least 0.1 cm$^2$/s.

In some implementations, platform 628 is formed from a dielectric or semi-conductive material having a high degree of thermal diffusivity, such as at least 1 cm$^2$/s. For example, in some implementations, the platform 628 is formed from at least one silicon-based material, such as silicon, silicon carbide, silicon nitride and the like. The high thermal diffusivity of the material forming the platform 628 more evenly or uniformly conducts or transfers heat generated on or within the platform to the surrounding fluid.

Because platform 628 is formed from a dielectric or semi-conductive material, the platform is well-suited for supporting electronic components or circuitry utilized to control heating element provided and the temperature sensor on the platform. In some implementations, the dielectric or semi-conductive material of the platform 628 facilitates the support of electronic circuitry utilized to control the heating element or the temperature sensor. In some implementations where the platform is formed from a semi-conductive material such as silicon, transistors or other electronic componentry may be directly formed in the platform, reducing the cost, complexity and size of the thermal processing device. In one implementation, the platform 628 has a width and a length of at least 10 times the width. The platform 628, formed as a "sliver", has a long length providing a large surface area for conducting heat to and away from the surrounding fluid.

Fluid heating elements 632 comprise individual elements that output heat. For example, in one implementation, each of fluid heating elements 632 may comprise an electrical resistor that outputs heat in response to being supplied with electrical current. In one implementation, each fluid heating element 632 is formed on an exterior surface of platform 628. In another implementation, each fluid heating element 632 is embedded within the layer or layers forming platform 628. In one implementation, fluid heating elements 632 collectively extend along at least 50% of a length of platform 628. In other words, the distance separating the first fluid heating element 632 of the series and the last fluid heating element 632 of the series is at least 50% of the length of platform 628. In another implementation, fluid heating element 632 collectively extend along at least 50% of the length of platform 628. In other implementations, the distance separating the first fluid heating element 632 of the series and the last fluid heating element 632 of the series is at least 75% of the length of platform 628. The heat emitted by heating elements 632 is absorbed by platform 628 and substantially uniformly diffused to the fluid within fluid chamber 644. In one implementation, heating elements 632 may be separated from the bulk material of platform 628 by a thin passivation layer; however, the thin passivation layer does not substantially interfere or interrupt the transfer of heat from the heating elements 632 to the bulk material of platform 628.

Temperature sensing elements 634 comprise individual elements that outputs signals indicating a temperature of the fluid within the fluid chamber. In one implementation, each temperature sensing element 634 may directly sense the temperature the fluid. In yet another implementation, each temperature sensing element 634 may indirectly sense the temperature of the fluid by sensing the temperature of a physical component or structure, the temperature of which is correlated to the temperature of the fluid. Temperature sensing elements 634 are independent of and distinct from heating elements 634. As a result, heating elements 632 and temperature sensing elements 634 may be independently located along platform 628, may be provided lower-cost distinct elements and may be independently controlled and monitored. In one implementation, each of temperature sensing elements 634 may comprise thermal temperature sense resistors. In one implementation, temperature sensing elements 634, collectively, extend along at least 50% of the length of platform 628. In other words, the distance separating the first temperature sensing element 634 of the series and the last temperature sensing element 634 of the series is at least 50% of the length of platform 628. In one implementation, temperature sensing elements 634, collectively, extend along at least 75% of the length of platform 628.

Although FIG. 8 illustrates a temperature sensing element 634 for each of heater elements 632, in other implementations, the number of heating elements 632 may be greater than the number of temperature sensing elements 634, or vice versa. Although heating elements 632 and temperature sensing elements 634 are illustrated as being insubstantial alignment with one another along the length of platform 628, in other implementations, heating elements 632 and temperature sensing elements 634 may be locationally offset or staggered relative to one another along the length of platform 628.

Enclosure 640 comprises a structure extending from substrate 624 at least partially around, over and about platform 628. Enclosure 640 extends within recess 714. In the example illustrated, enclosure 640 is U-shaped, having a channel facing lower body 706 form fluid chamber 644. In the example illustrated, enclosure 640 may be formed from a transparent material to form an at least partially transparent chamber to facilitate viewing of the fluid sample within an along a length of enclosure 640, to facilitate use with an off-tool/off-chip optical sensor, or to serve as a light transmitting light pipe. In one implementation, enclosure 640 may be formed from a transparent material such as glass or a transparent polymer. In other implementations, enclosure 640 may be formed from other materials or may be opaque. For example, electrical detection may benefit from an opaque lid or opaque chamber.

As shown by FIG. 8, enclosure 640 terminates prior to reaching end wall 716 of recess 714, forming an opening or inlet 720 into the space between lower body 706 and enclosure 640 that forms chamber 644. The edge of inlet 720 may be angled or straight. The mouth or inlet 720 may have a diameter of less than or equal to the capillary length of the fluid to be drawn up through capillary action. In one implementation, inlet 720 may have an opening dimension of less than or equal to 6 mm (based upon the capillary length of water). In other implementations, the size of inlet 720 is one that provides for capillary rise (pursuant to Jurin's law) within and along the chamber 644, from inlet 720 to all of the fluid interaction elements 632 and 634.

In one implementation, interior surfaces 724 of the enclosure 640 and the floor surfaces 728 of lower body 706 are formed from a material that is completely wetted with the fluid being drawn up through inlet 720. In other words, such surfaces 724 and 728 are fluid-philic with respect to the fluid that is being drawn up. In one implementation, the surfaces 724 and 728 comprise a material such as polyetherimide (PEI), or liquid-crystal-polymer (LCP). In some implementations, the surfaces 724 and 728 may be formed by an over-molded material. In some implementations, the interior surfaces 724 and 728 may be coated with a metal such as gold. In one implementation, lower body 706 and the enclosure 640 may be fabricated out of an injectable moldable plastic, wherein a layer of metal (hydrophilic relative to plastic such as polypropylene) is electrolitically plated over the plastic. In another implementation the enclosure 640 and lower body 706 may be fabricated out of an injectable moldable plastic, wherein a layer of metal (hydrophilic relative to plastic such as polypropylene) is electrolytically plated over the plastic. In some implementations, the interior surfaces 724 and 728 may be formed from other less hydrophilic materials such as polypropylene. In yet other implementations, the interior surfaces 724 and/or 728 may be formed from printed circuit board materials, such as a glass-reinforced epoxy laminate material, sometimes referred to as FR4.

As shown by FIG. 9, enclosure 640 cooperates with substrate 624 to form a fluid chamber 644 having a volume of uniform thickness that conforms to and about platform 628. This uniform thickness conforms to platform 628 in at least first and second dimensions, wherein fluid may exit and/or enter the fluid chamber in the third dimension. In the example illustrated, this uniform thickness may conform to platform 628 along the top and sides of platform 628. Because the volume of fluid chamber 644 has a uniform thickness conforming to and about the platform 628, heat generated by or on the platform 628, and conducted by the platform 628 to the surrounding fluid more uniformly heats the fluid within the volume. As a result, the temperature of the fluid is more rapidly and uniformly elevated. Likewise, the temperature the fluid may be more rapidly and uniformly cooled. Thus, thermal cycling is faster and efficient.

In some implementations, the uniform thickness of the volume or gap that conforms to and about the platform is no greater than 200 μm. This spacing may facilitate uniform heating of the fluid within the volume or gap to temperatures that may be utilized as part of a thermal cycling process by heating elements, such as electrical resistors that may be supported upon the platform. For example, the uniform thickness of the gap may facilitate uniform heating of a fluid, such as a sample reagent mixture for which a targeted nucleic acid is being detected, to a temperature of at least 90° C. for thermal cycling. In some implementations, depending upon the heating elements, the uniform thickness may be greater than 200 μm.

In one implementation, enclosure 640 is integrally formed as a single unitary body. In yet other implementations, enclosure 640 is formed from multiple sections, segments or panels bonded, welded, fastened or otherwise joined to one another. In one implementation, enclosure 640 is formed from the same material as that of substrate 624. In other implementations, enclosure 640 may be formed from a material distinct from that of substrate 624. In some implementations, enclosure 640 comprises side wall portions and a lid that forms an interior surface of the fluid chamber opposite substrate 624. In such an implementation, the lid portion of enclosure 640 may have a thickness of at least 50 micrometers, and in some implementations, up to 1000 μm, where such a thickness reduces thermal cycling time by facilitating faster cooling/convective heat transfer.

In operation, controller 650 (or remote controller) may output control signals activating fluid heating elements 632 that are submersed in a fluid to be thermally processed. Signals from the temperature sensors 634 are communicated to controller 650 (or the remote controller) and wherein the controller 650 (or remote controller) adjusts and controls the operation of the fluid heating elements 632 based upon the sensed temperatures received from the individual temperature sensing element 634. In one implementation, controller 650 (or the remote controller) may utilize signals from the temperature sensing fluid interaction elements to selectively activate the fluid heating element 632 so as to thermal cycle the sample fluid, such as for a PCR process. In one implementation, controller 650 (or the remote controller) may differently heat the fluid in the different zones provided by the independently controllable and activatable fluid heating element 632.

Although the present disclosure has been described with reference to example implementations, workers skilled in the art will recognize that changes may be made in form and detail without departing from the spirit and scope of the claimed subject matter. For example, although different example implementations may have been described as including features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. A fluid thermal processing device comprising:
a substrate;
a platform projecting from the substrate;
a fluid heating element supported by the platform;
a temperature sensing element, distinct from the fluid heating element, supported by the platform; and
an enclosure supported by the substrate and cooperating with the substrate to form a fluid chamber of uniform thickness around the platform, wherein the platform, the fluid heating element, and the temperature sensing element are exposed to the fluid chamber.

2. The fluid device of claim 1, wherein the platform is formed from at least one silicon-based material.

3. The fluid device of claim 1, wherein the platform consists of at least one silicon-based material.

4. The fluid device of claim 1, wherein the platform has a thermal diffusivity of at least 0.05 cm$^2$/s.

5. The fluid device of claim 1, wherein the platform has a width and a length of at least 10 times the width.

6. The fluid device of claim 5, wherein the temperature sensing element extends along at least 50% of the length.

7. The fluid device of claim 5, wherein the fluid heating element extends along at least 50% of the length.

8. The fluid device of claim 1, wherein the fluid heating element is one of a plurality of fluid heating elements along a length of the platform, each of the plurality of fluid heating elements being independently controllable to provide distinct heating zones along the length of the platform.

9. The fluid device of claim 8, wherein the temperature sensing element is one of a plurality of temperature sensing elements along the length of the platform, each of the plurality of temperature sensing elements to output independent temperature measurements along the length of the platform.

10. The fluid device of claim 1, wherein the enclosure comprises a lid, having a lid thickness of at least 50 μm and no greater than 1000 cm$^2$/s.

11. The fluid device of claim 1 further comprising a controller, the controller being supported by the substrate to output control signals causing the fluid heating element to thermal cycle fluid within the fluid chamber.

12. A fluid thermal processing method comprising:
supplying a fluid into a fluid chamber of a fluid thermal processing device, the fluid thermal processing device comprising a substrate, a platform projected from the substrate and supporting a fluid heating element and a temperature sensing element each exposed to the fluid chamber, and the fluid chamber having a substantially uniform thickness around the platform;
heating the fluid within the fluid chamber around the platform with the fluid heating element supported by the platform; and
sensing a temperature of the fluid around the platform with the temperature sensing element distinct from the fluid heating element and supported by the platform.

13. The fluid thermal processing method of claim 12, wherein the platform comprises a silicon-based material.

14. The fluid thermal processing method of claim 12, wherein the fluid comprises a nucleic acid sequence and a DNA synthesis enzyme and wherein the fluid within the fluid chamber is heated with the fluid heating element to at least one controlled temperature, as sensed by the temperature sensing element, so as to duplicate the nucleic acid sequence.

15. A fluid thermal processing stick comprising:
a first end supporting an electrical interconnect to be operatively coupled to a controller; and
a second end forming a fluid interactor, the fluid interactor comprising:
a platform supported by a substrate and having a width and a length, the length being at least 10 times the width;
a heating element supported by the platform and under control of the controller;
a temperature sensing element distinct from the heating element and supported by the platform to output temperature measurements to the controller; and
an enclosure supported by and cooperating with the substrate to form a fluid chamber about the platform, the fluid chamber having a uniform thickness around the platform, wherein the platform, the heating element, and the temperature sensing element are exposed to the fluid chamber within the enclosure.

16. The fluid device of claim 1, wherein the fluid chamber includes a substantially equal spacing between a first portion of an exterior surface of the platform and a second portion of an interior surface of the enclosure that is opposite the first portion.

17. The fluid device of claim 1, wherein the temperature sensing element and the fluid heating element are independently located along the platform and are independently controlled.

18. The fluid thermal processing method of claim 12, wherein supplying the fluid into the fluid chamber and heating the fluid further includes contacting a portion of the fluid to an exterior surface of the platform and conducting heat generated by the fluid heating element to the fluid, wherein the volume has the substantially uniform thickness conforming to and extending about the platform in a first dimension and a second dimension.

19. The fluid thermal processing stick of claim 15, wherein the platform is to diffuse heat generated by the heating element to fluid within the fluid chamber, the fluid being in contact with an exterior surface of the platform, and the fluid chamber forming the volume of uniform thickness including a substantially equal spacing between a first portion of the platform and a second portion of the enclosure.

20. The fluid thermal processing stick of claim 15, wherein the temperature sensing element and the heating element are independently under control of the controller.

* * * * *